US006191126B1

(12) United States Patent
Gamache

(10) Patent No.: US 6,191,126 B1
(45) Date of Patent: Feb. 20, 2001

(54) TOPICAL USE OF κ OPIOID AGONISTS TO TREAT OCULAR PAIN

(75) Inventor: Daniel A. Gamache, Arlington, TX (US)

(73) Assignee: Alcon Laboratories, Inc., Fort Worth, TX (US)

( * ) Notice: Under 35 U.S.C. 154(b), the term of this patent shall be extended for 0 days.

(21) Appl. No.: 09/319,064

(22) PCT Filed: Dec. 11, 1997

(86) PCT No.: PCT/US97/23185

§ 371 Date: May 27, 1999

§ 102(e) Date: May 27, 1999

(87) PCT Pub. No.: WO98/26770

PCT Pub. Date: Jun. 25, 1998

Related U.S. Application Data

(60) Provisional application No. 60/032,909, filed on Dec. 16, 1996.

(51) Int. Cl.$^7$ ................................................... A61K 31/55
(52) U.S. Cl. ................ 514/211.12; 514/413; 514/433; 514/912; 514/213.01
(58) Field of Search .............................. 514/413, 213.01, 514/433, 912, 211.12

(56) References Cited

U.S. PATENT DOCUMENTS

| | | | |
|---|---|---|---|
| 4,939,135 | 7/1990 | Robertson et al. | 514/179 |
| 5,049,669 | 9/1991 | Garret et al. | 514/226.2 |
| 5,270,050 | 12/1993 | Coquelet et al. | 424/427 |
| 5,401,510 | 3/1995 | Robertson et al. | 424/427 |
| 5,688,955 | 11/1997 | Kruse et al. | 546/276.4 |

FOREIGN PATENT DOCUMENTS

| | | |
|---|---|---|
| 0 346 238 A1 | 12/1989 | (EP) . |
| 0 657 443 A1 | 6/1995 | (EP) . |
| WO 94/13275 A1 | 6/1994 | (WO) . |
| WO 98-26770 | 6/1998 | (WO) . |

OTHER PUBLICATIONS

Barber, et al., "A pharamacological profile of the novel, peripherally–selective κ–opioid receptor agonist, EMD 61753", *British Journal Of Clinical Pharmacology*, vol. 113, No. 4, pp. 1317–1327 (1994).

DeHaven–Hudkins et al., "A Peripherally Slective Opiate Analygesic", *Society For Neuroscience*, vol. 22, p. 1362, abstract No. 540.1 (1996).

Eisenberg, et al., "The peripheral antinociceptive effect of morphine in a rat model of facial pains", *Neuroscience*, vol. 72, No. 2, pp. 519–525 (1996).

*Goodman and Gilman's Pharmacological Basis of Therapeutics* (8th Edition), Jaffee, Chapter 21: "Opioid Analgesics And Antagonists", pp. 485–492 (1993).

Gottschlich, et al., "The peripherally acting κ–opiate agonist eMD 61753 and analogues: opioid activity versus peripheral selectivity", *Drugs Exptl. Clin. Res.*, vol. XX1(5), pp. 171–174 (1995).

Joris et al., "Opiates suppress carrageenan–induced edema and hypothermia at doses that inhibit hyperalgesia", *Pain*, vol. 43, No. 1, pp. 95–103 (1990).

Kanemasa, "κ–Opioid agonist U50488 inhibits P–type $Ca^{2+}$ channels by two mechanisms", *Brain Research*, vol. 707, pp. 207–212 (1995).

Ueda, et al., "Dual Effects of Dynorphin–1(1–13) on Cholinergic and Substance P–ergic Transmissions in the Rabbit Iris Sphincter Muscle", *J. Pharmacol. Exp. Ther.*, vol. 232, No. 2, pp. 545–550 (1985).

*Primary Examiner*—Zohreh Fay
(74) *Attorney, Agent, or Firm*—Michael C. Mayo; Patrick M. Ryan

(57) ABSTRACT

The present invention relates to the pharmaceutical treatment of pain. In particular, the present invention relates to the topical use of kappa opioid receptor agonists and partial agonists for the prevention or alleviation of pain in the eye.

4 Claims, No Drawings

TOPICAL USE OF κ OPIOID AGONISTS TO TREAT OCULAR PAIN

This application claims benefit of Provisional application No. 06/032,909, filed Dec. 16, 1996, and this application is a 371 of PCT/US97/23185, filed Dec. 11, 1997.

BACKGROUND OF THE INVENTION

Pain is a perceived nociceptive response to local stimuli in the body. The perception of pain at the level of the central nervous system requires the transmission of painful stimuli by peripheral sensory nerve fibers. Upon stimulation of tissue (i.e., thermal, mechanical or chemical), electrochemical signals are transmitted from the sensory nerve endings to the spinal column, and hence to the brain where pain is perceived.

The cornea is highly innervated with sensory afferents which transmit various painful stimuli to the central nervous system. Pain conditions involving the eye, therefore, can arise in numerous instances, such as: foreign body stimulus, inflammation, dry eye syndrome, accidental trauma, surgical procedures and post-surgical recovery. For example, ocular pain can result from photorefractive keratotomy ("PRK"), a vision correcting, surgical procedure whereby a laser is used to shape the cornea. This process involves the photoablation of Bowman's membrane and the stromal levels of the cornea. As a result, the denuding of the nerve-containing epithelial layers of the cornea can cause some patients to experience pain following laser surgery until the epithelium regenerates.

Various therapies have been attempted for the alleviation of pain. The use of non-steroidal anti-inflammatory drugs (NSAIDs), such as diclofenac, have been developed to treat pain. These agents inhibit cyclooxygenase dependent prostaglandin synthesis. Prostaglandins can modulate pain perception at the level of the central nervous system and systemic administration of NSAIDs is known to provide analgesia. However, the use of NSAIDs can involve undesired side effects including gastrointestinal bleeding and kidney dysfunction.

Local anesthetics are another class of pain modulators which relieve pain by directly inhibiting nerve cellular function. One problem with local anesthetic therapy is that the anesthetics exhibit a short duration of action. Another problem with the use of local anesthetics is that their mechanism of action, non-specific membrane stabilization, can have the undesired coincident effect of also inhibiting biological functions of other cells, such as fibroblasts and surrounding neural cells. Therefore, even though pain sensation can be abated with local anesthetic treatment, healing and normal function of the tissue may be significantly compromised. There is a need, therefore, to discover agents which potently and specifically inhibit the transmission of painful stimuli by sensory afferents, without local anesthetic activity, following topical ocular application.

Other agents have also been suggested for use in treating pain. Such agents include tricyclic antidepressants such as imipramine and desipramine, alpha-2 adrenergic agonists, serotonin uptake blockers, such as prozac, and other analgesics such as paracetamol, as described in U.S. Pat. No. 5,270,050 (Coquelet et al.). Some of these therapies, however, have been associated with side-effects such as dryness of mouth, drowsiness, constipation, and low potencies and efficacies.

Opiates are another class of compounds used to treat pain. Opiates can be administered in a number of ways. For example, opiates can be administered systematically, by intravenous injection or oral dosage, or locally, by subcutaneous, intramuscular or topical application. Systemic administration of opiates, however, has been associated with several problems including dose escalation (tolerance), addiction, respiratory depression and constipation.

"Opioids" is a generic term of art used to describe molecules that produce morphine-like activity in the body. Opioid receptors are membrane proteins which generally cause analgesic responses when bound by opioids. There are three major categories of opioid receptors, designated μ (mu), κ (kappa) and δ (delta). Other sub-type receptors appear to exist as well. Opioid receptors have been differentiated among each other by the preferential binding affinities of different agonists and antagonists, and by the different responses obtained from each receptor's binding. For example, the full agonist morphine has a ten times greater affinity for the mu receptor than for the delta and kappa receptors. Thus, morphine is a mu agonist (See, *Goodman and Gilman's Pharmacological Basis of Therapeutics* (8th Edition), Jaffee, Chapter 21: *Opioid Analgesics And Antagonists*, page 485–492 (1993).) Kappa receptors have also been delineated from the general class of opioid receptors by the fact that mu and delta receptor agonists increase membrane potassium conductance and decrease the duration of presynaptic action potential, whereas kappa receptor agonists decrease voltage-dependent calcium conductance without affecting potassium conductance (Kanemasa, *k-opioid agonist U50488 inhibits P-type $Ca^{2+}$ channels by two mechanisms, Brain Research*, volume 707, pages 207–212 (1995)).

While it is known that opiate analgesics such as morphine relieve pain by activating specific receptors in the brain, recent studies demonstrate the analgesic effects of compounds which act on kappa receptors in peripheral tissue. (See, Joris et al., *Opiates suppress carrageenan-induced edema and hypothermia at doses that inhibit hyperalgesia, Pain*, volume 43, pages 95–103 (1990); Eisenberg, *The peripheral antinociceptiave effect of morphine in a rat model of facial pains, Neuroscience*, volume 72, No. 2, pages 519–575 (1996); and Gohschlich, *The peripherally acting k-opiate agonist EMD 61753 and analogues: opioid activity versus peripheral selectivity, Drugs Exptl. Clin. Res.*, volume XX1(5), pages 171–174 (1995)).

SUMMARY OF THE INVENTION

The present invention is directed to compositions and methods of treating ocular pain. The present invention is based in part on the finding that compounds which bind to kappa opioid receptors in the eye inhibit ocular pain. More specifically, the present invention provides compositions containing kappa opioid agonists for the treatment of ocular pain.

The methods of the present invention involve the topical dosage of the compositions described below. One advantage of this therapy is that the inhibition of pain is receptor-specific, as contrasted with non-specific therapy, such as local anesthetic treatment. This specific activity may reduce greatly the number of dosings per day, and also reduce other drawbacks such as short duration of action and inhibition of wound healing, which are associated with local anesthetics. Additionally, kappa opioid receptor binding agents acting locally within ocular tissue avoid the problems of tolerance, addiction and constipation associated with the chronic, systemic administration of opiates.

DETAILED DESCRIPTION OF THE INVENTION

The present invention is directed to the use of kappa opioid receptor agonists for the prevention or alleviation of pain. It has now been found that kappa opioid agonists potently prevent or alleviate ocular pain. The kappa opioid receptor is found principally in the spinal cord, but recent evidence of other peripherally located kappa receptors has been reported, as described above.

The compounds of the present invention are kappa opioid receptor agonists. As used herein, a "kappa opioid agonist" refers to a compound which activates a kappa opioid receptor. Other opioid receptor agonists, such as mu and delta are excluded from the present invention compounds.

The kappa opioid receptor agonists of the present invention are known or may be elucidated by various biological binding studies known in the art. For example, the kappa opioid agonists of the present invention may be ascertained by displacement studies involving the binding of known radioactive agonists, such as U69593, with target tissue slices or homogenates (Gohschlich, *Drugs Exptl. Clin. Res.*, Volume XX1(5), pages 171–174 (1995)).

The following compounds are examples of kappa opioid agonists, listed as their trade name/number: enadoline, ICI-199441, R-84760, ZT-52656A, tifluadom, PD-117302, PD-129290, MR-1268, KT-90, GR45809, GR-89696, GR-103545, GR-45809, GR-94839, xorphanol, RU49679, fedotozine, DuP-747, HN-11608, RP-60180 U-69593, U-62066 spiradoline mesylate, and trans-U-50488 methane sulfate. Preferred kappa opioid compounds of the present invention are those which only act in the periphery and do not cross the blood-brain barrier, or have limited CNS effects, such as EMD-60400 and EMD 61753. The most preferred kappa opioid agonist is EMD-61753. The kappa opioid agonists of the present invention are available from commercial sources or may be synthesized by methods known to those skilled in the art.

The following is an example of the ocular anti-pain efficacy of representative kappa opioid receptor agonists of the present invention, as compared with other agents:

EXAMPLE 1

Representative compounds of the present invention, a mu agonists (morphine) and a local anesthetic (Alcaine®, Alcon Laboratories, Inc, Fort Worth, Tex.) were tested in a formalin-induced model of ocular pain in the rat. Briefly, 20 µL of the compound to be tested or vehicle (maxidex vehicle) were applied topically at various times between 1 and 30 minutes prior to the administration of formalin. 5 µL of a 0.1% w/v formalin solution (5 µg) was then topically applied using an eppendorf pipette. Blinking began immediately and the frequency over the first minute was determined. The 5 µg dose of formalin typically yielded about 40–50 blinks in the first minute. The control counts of vehicle animals were compared to the counts of dosed animals and percent inhibition was then calculated. The results are illustrated in Table 1 below:

TABLE 1

| Compound | Type | % w/v | % Inhibition |
| --- | --- | --- | --- |
| Alcaine | local anesthetic | 0.5 | 94 |
| GR 89696 | kappa opioid agonist | 0.1 | 98 |
| U-69593 | kappa opioid agonist | 0.1 | 63 |
| U-62066 spiradoline mesylate | kappa opioid agonist | 0.1 | 68 |
| trans-U-50488 methane sulfate | kappa opioid agonist | 0.1 | 64 |
| Morphine | mu opioid agonist | 1.0 | 8 |

As can be seen from Table 1, the topical administration of kappa opioid agonists was effective in inhibiting ocular pain in the rat, in contrast to the topical administration of the mu agonist, morphine.

The kappa opioid agonists of the present invention will be contained in compositions, in accordance with formulation techniques known to those skilled in the art. The compounds may be included in solutions, suspensions and other dosage forms adapted for the particular kappa opioid agonist and dosing regimen.

The present invention is particularly directed to the provision of compositions adapted for topical treatment of ophthalmic tissues. The ophthalmic compositions of the present invention will include one or more kappa opioid agonists and a pharmaceutically acceptable vehicle for these agonist(s). Various types of vehicles may be used. The vehicles will generally be aqueous in nature. Aqueous solutions or suspensions are generally preferred, based on ease of formulation, as well as a patient's ability to easily administer such compositions by means of instilling one to two drops of the solutions in the affected eyes. However, the compounds of the present invention may also be readily incorporated into other types of compositions, such as suspensions, viscous or semi-viscous gels or other types of solid or semi-solid compositions. Suspensions may be preferred for kappa opioid agonists which are relatively insoluble in water. The ophthalmic compositions of the present invention may also include various other ingredients, such as buffers, preservatives, co-solvents and viscosity building agents.

An appropriate buffer system (e.g., sodium phosphate, sodium acetate or sodium borate) may be added to prevent pH drift under storage conditions.

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, polyquaternium-1, or other agents known to those skilled in the art Such preservatives are typically employed at a level of from 0.001 to 1.0 percent by weight, based on the total weight of the composition (wt. %).

Some of the compounds of the present invention may have limited solubility in water and therefore may require a surfactant or other appropriate co-solvent in the composition. Such co-solvents include: polyethoxyiated castor oils, Polysorbate 20, 60 and 80; Pluronic® F-68, F-84 and P-103 (BASF Corp., Parsippany N.J., USA); cyclodextrin; or other agents known to those skilled in the art. Such co-solvents are typically employed at a level of from 0.01 to 2 wt. %.

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from 0.01 to 2 wt. %.

The compounds may also be used for treating irritated tissues following ophthalmic surgery. The compounds may be used for acute treatment of temporary conditions, or may be administered chronically. The compounds may also be used prophylactically, especially prior to ocular surgery or noninvasive ophthalmic procedures, or other types of surgery.

The compounds and compositions of the present invention will be used to prevent or ameliorate ocular pain associated with various stimuli. For example, the kappa opioid agonists and compositions of the present invention may be used in treating pain arising from allergens, inflammation, trauma, dry eye, foreign body sensation, such as from contact lenses and surgery. The compounds of the present invention may be used for the treatment of pain following ocular surgery, such as PRK surgery. With such treatment, the kappa opioid agonists can be individually dosed, or in combination with other pharmaceutical agents such as by methods disclosed in U.S. Pat. Nos. 4,939,135 and 5,401,510 (Robertson et al.), the entire contents of which are incorporated herein by reference. The compounds will be utilized in a concentration effective to prevent or ameliorate ocular pain. As used herein, the term "pharmaceutically effective amount" refers to that amount of one or more kappa opioid agonists which prevents or alleviates ocular pain. In general, the dosage of kappa opioid agonists utilized for any of the above-described purposes will generally be from about one to two drops of a 0.01 wt. % to 3 wt. % composition, administered one to four times per day.

The compositions of the present invention are farther illustrated by the following formulation Examples 2–4. The ingredient "kappa opioid agonist" denotes a compound of the present invention.

EXAMPLE 2

| Ingredient | Amount (wt %) |
| --- | --- |
| EMD-61753 | 0.01–1.0% |
| Phosphate Buffered Saline | 1.0 |
| Polysorbate 80 | 0.5 |
| Purified water | q.s. to 100% |

EXAMPLE 3

| Ingredient | Amount (wt %) |
| --- | --- |
| kappa opioid agonist | 0.01–1.0% |
| Monobasic sodium phosphate | 0.05 |
| Dibasic sodium phosphate (anhydrous) | 0.15 |
| Sodium chloride | 0.75 |
| Disodium EDTA (Edetate disodium) | 0.05 |
| Cremophor EL | 0.1 |
| Benzalkonium chloride | 0.01 |
| HCl and/or NaOH | pH 7.3–7.4 |
| Purified water | q.s. to 100% |

EXAMPLE 4

| Ingredient | Amount (wt %) |
| --- | --- |
| kappa opioid agonist | 0.01–1.0% |
| Phosphate Buffered Saline | 1.0 |
| Hydroxypropyl-β-cyclodextrin | 4.0 |
| Purified water | q.s. to 100% |

What is claimed is:

1. A method for treating ocular pain which comprises topically administering to a human eye a composition comprising a pharmaceutically effective amount of one or more kappa opioid agonist(s) in a pharmaceutically acceptable vehicle.

2. A method according to claim 1, wherein the kappa opioid agonist is selected from the group consisting of: asimadoline (EMD-61753); enadoline; benzeneacetamide, 3,4-dichloro-N-methyl-N-[1-phenyl-2-(1pyrroldinyl) ethyl]-, monohydrochloride, (S)-(ICI-199441); thiomorpholine, 4-[(5,6-dichloro-2,3-dihydro-1H-inden-1yl)carbonyl]-3-(1-pyrrolidinylmethyl)-, monohydrochloride, [R-($R^+$,$S^+$)]-(R-84760); piperidine, 2-(1-pyrrolidinylmethyl)-1-[[4-(trifluoromethyl)phenyl] acetyl]-, monohydrochloride, (S)-(ZT-52656A); tifluadom; benzo[b]thiophene-4-acetamide, N-methyl-N-[2-(1-pyrrolidinyl)cyclohexyl]-, monohydrochloride, trans-(+/−)-(PD-117302); 4-benzofuranacetamide, N-methyl-N-[7-(1-pyrrolidinyl)-1-oxaspiro[4,5]dec-8-yl]-, monohydrochloride, [5R-(5.alpha.,7.alpha.,8.beta.)]-(PD-129190); 2,6-methano-3-benzazocin-8-ol, 1,2,3,4,5,6-hexahydro-6,11-dimethyl-3-[(2-methyl-3-furanyl)methyl]-, (2alpha,6alpha,11R*)-(+/−)-(MR-1268); morphinan-3-ol,6-(acetylthio)-17-(cyclopropylmethyl)-7,8-didehydro-4,5-epoxy-, acetate(ester), (5alpha,6beta)-(KT-90); 1,4-dioxa-8-azaspiro[4,5]decane, 8-[(3,4-dichlorophenyl)acetyl]-7-(1-pyrrolidinylmethyl)-, monohydrochloride (GR-45809); 1-piperazinecarboxylic acid, 4-[(C3,4-dichlorophenyl) acetyl]-3-(1-pyrrolidinylmethyl)-, methyl ester, (E)-2-butenedioate (GR-89696); (R)-methyl-4-[(3,4-dichlorophenyl)acetyl]-3-(1-pyrrolidinyl-methyl)-1-piperazinecarboxylate fumarate (GR-103545); piperazine, 4-acetyl-1-[(3,4-dichlorophenyl)acetyl]-2-[(3-hydroxy-1-pyrrolidinyl)methyl](GR-94839); xorphanl; benzeneacetamide, N-[2,3-dihydro-2-(1-pyrrolidinyl)-1H-inden-1-yl]-N-methyl-3-nitro-, monohydrochloride, trans-(+/−)-(RU-49679); fedotozine; benzeneacetamide, 3,4-dichloro-N-methyl-N-[1,2,3,4-tetrahydro-5-methoxy-2-(1-pyrrolidinyl)-1-naphthalenyl]-, trans-(+/−)-(DuP-747); (E)-4,5-dichloro-N-methyl-N-[2-[1-pyrrolidinyl]cyclohexyl]-2-thiopheneacetamide HCl (HN- 11608); apadoline (RP-60180); spiradoline mesylate; and benzeneacetamide, 3,4-dichloro-N-methyl-N-[2-(1-pyrrolidinyl)cyclohexyl]-, trans-(+/−)-, monomethanesulfonate (trans-U-50488 methane sulfate).

3. A method according to claim 2, wherein the kappa opioid agonist is asimadoline (EMD-61753).

4. A method according to claim 2, wherein the ocular pain is the result of PRK surgery.

* * * * *